United States Patent [19]

Faunce

[11] 4,292,306
[45] Sep. 29, 1981

[54] DENTIFRICE WITH TOPICAL AND SYSTEMIC PHOSPHATE FLUORIDE SYSTEM

[76] Inventor: Frank R. Faunce, 201 Wilcrest Dr., Apt. 946, Houston, Tex. 77042

[21] Appl. No.: 92,277

[22] Filed: Nov. 8, 1979

Related U.S. Application Data

[62] Division of Ser. No. 973,910, Dec. 28, 1978, Pat. No. 4,203,966.

[51] Int. Cl.$^3$ ............................................. A61K 7/18
[52] U.S. Cl. ...................................... 424/52; 424/57
[58] Field of Search .................................. 424/52, 57

[56] References Cited

U.S. PATENT DOCUMENTS

| | | | |
|---|---|---|---|
| 1,691,504 | 11/1928 | Vogt | 424/57 |
| 2,216,816 | 10/1940 | Kuever | 424/57 |
| 3,282,792 | 11/1966 | Fiscella | 424/52 |
| 3,431,339 | 3/1969 | Gyarmathy et al. | 424/57 |
| 3,445,567 | 5/1969 | Muhler | 424/52 |
| 3,475,533 | 10/1969 | Mayrand | 424/57 |
| 3,574,824 | 4/1971 | Echeandia et al. | 424/50 |
| 3,577,521 | 5/1971 | Scheller et al. | 424/57 |
| 3,689,637 | 9/1972 | Pader | 424/52 |
| 3,892,843 | 7/1975 | Muhler et al. | 424/52 |
| 3,919,409 | 11/1975 | Perla et al. | 424/52 |
| 3,927,202 | 12/1975 | Harvey et al. | 424/57 |
| 3,929,987 | 12/1975 | Cocodney et al. | 424/52 |
| 4,002,732 | 1/1977 | Gault | 424/49 |
| 4,069,311 | 1/1978 | Mannara | 424/49 |
| 4,071,614 | 1/1978 | Grimm | 424/49 |
| 4,071,615 | 1/1978 | Barth | 424/52 |
| 4,082,841 | 4/1978 | Pader | 424/50 |
| 4,132,771 | 1/1979 | Schreiber et al. | 424/52 |
| 4,169,885 | 10/1979 | Raaf et al. | 424/16 |
| 4,196,189 | 4/1980 | Raaf et al. | 424/37 |
| 4,198,394 | 4/1980 | Faunce | 424/52 |
| 4,203,966 | 5/1980 | Faunce | 424/52 |

FOREIGN PATENT DOCUMENTS 1222197 2/1971 United Kingdom .
1408922 10/1975 United Kingdom .

OTHER PUBLICATIONS

Friberger, P., Chem. Abstr. 82, #64398m (1975), of Sven. Tandlaek. Tidskr., (1974)67(4):193-198, Fluoride Uptake from Prophylactic Dentifrices III, in Uitro Fluoride Uptake in Tooth Enamel from an Acidulated Phosphate Dentifrice of Bofors Toothpaste Type.

Primary Examiner—Shep K. Rose
Attorney, Agent, or Firm—Gunn, Lee & Jackson

[57] ABSTRACT

A coated fluoride and a stannous fluoride containing dentrifice of a mixture containing sodium dihydrogen phosphate, calcium pyrophosphate, glycerin, sodium carboxymethylcellulose, xylitol, distilled water and spearmint oil. The dentifrice is preferably in the form of a gel.

1 Claim, No Drawings

DENTIFRICE WITH TOPICAL AND SYSTEMIC PHOSPHATE FLUORIDE SYSTEM

This is a division of application Ser. No. 973,910, filed Dec. 28, 1978, now U.S. Pat. No. 4,203,966.

BACKGROUND OF THE INVENTION

This invention relates to a dentifrice composition. More particularly, it relates to a toothpaste composition in gel form that contains fluoride and which is ingestible, non-burning and non-foaming.

In general, a dentifrice is a substance for cleaning the surfaces of the teeth when used in conjunction with a toothbrush. They are available as powders and pastes and contain flavoring agents, sweetening agents, soaps or detergents, and abrasives. It is the purpose of a dentifrice to free the teeth of stain, tartar, calculus and acid plaque.

Powder dentifrices are more abrasive than the paste type. Therefore, their use is more or less limited to teeth requiring stronger than average scrubbing. Paste dentifrices, however, avoid excessive tooth wear which is inherent in the powder type dentifrice.

In order to fight or inhibit tooth decay, it has been common practice to add fluoride to the dentifrice. This has generally taken the form of stannous fluoride, which is an added ingredient in many commercial brands of toothpaste.

Other attempts to prevent tooth decay have embodied the addition to the dentifrice of such compositions as hexachlorophene, which is a sterilizing agent, N-lauroyl sarcosinate, which is a suger-fermentation preventative, and urea, which is an enzyme. But the most effective tooth decay inhibitor has been found to be fluoride, as hereinbefore stated.

In the past, bicarbonate of soda has found widespread use as a dentifrice. This material possesses the proper degree of grittiness and, hence, serves the abrasive function of removing stains from the teeth. It suffers, however, from the disadvantage of lacking a refreshing flavor.

It has therefore become common practice to add to a dentrifrice composition mint flavors or chlorophyll. When used in conjunction with a dentifrice, these materials provide a flavorful and refreshing after-effect which makes brushing pleasant. In addition, flavoring agents minimize or combat to some degree halitosis and remove the odors of alcohol, smoke and certain foods.

The most preferable dentifrice should prevent tooth decay, prevent bad breath, clean the teeth, polish the teeth, leave no unpleasant aftertaste, and be responsible for no harmful effects on the teeth or the tender surfaces of the mouth, tongue and lips. It should also be of a nature to be harmless if swallowed.

Paste and powder dentifrices generally include the same ingredients. The paste type dentifrice, however, in addition includes a binder material and a lubricant material. The binder functions to hold the solid substances of the various ingredients together in a more or less plastic mass. The lubricant functions to ease elimination of the paste from the tube.

Many different forms of paste dentifrices have been devised and made available for brushing the teeth, although most of these compositions may be characterized as either a "burning-type" paste dentifrice or a "foaming-type" paste dentifrice, or both. What has not been generally appreciated in the various disadvantages attendant to these burning and foaming type paste dentifrices.

Thus, many people, especially children, dislike using toothpastes for the reason that if some of the dentifrice is swallowed during the brushing sequence, a burning or unpleasant feeling is induced in the stomach. This burning sensation is due to the presence of the detergent in the dentifrice composition. The detergent is also responsible for the somewhat unpleasant burning effect that the dentifrice has on the sensitive tissues of the mouth, tongue and lips. This burning effect in the mouth may vary from slight effects to, at times, acute burning sensations. It is one of the reasons why some people resist toothbrushing, a function badly needed by all persons in order to preserve their teeth.

Another drawback of conventional paste dentifrices is that the use of water is required for brushing. This combination of water and the paste dentifrice results in an effect termed "foaming." Thus, during the brushing sequence a foam is produced. This foam renders it difficult to maintain the dentifrice in the mouth during the brushing operation and causes dribbling of the dentifrice out of the mouth of the user. This accounts for spillage of the dentifrice about the bath facilities and upon floors and clothing. The foaming effect of the dentifrice also entails the disadvantage that rinsing of the mouth with water is required at the end of the brushing sequence. This requires the presence of a glass of water at hand, or for the user to draw water into the mouth from the faucet of the facility. The presence of glassware in a bathroom facility is disadvantageous due to the hazard of breakage. The drawing of water into the mouth from the faucet of the facility possesses the disadvantage that often these faucets are unsanitary, and therefore the placing of the mouth near or about the faucet is undesirable, or a water source is unavailable.

A further drawback of foaming type dentifrices that require water and rinsing can be understood when the case of school children, hospitalized patients, handicapped people, or invalids is considered. Since it is difficult, if not impossible, for these people to be up and about, the requirement of water to brush and rinse makes the toothbrushing function more than difficult. Thus, access to a bath facility including water is not available to them, and therefore if the teeth are to be brushed at all, some water supply must be carried to them which becomes burdensome and messy.

Another disadvantage of the foaming type dentifrices is the fact that during the brushing operation many bubbles are produced in the foaming process, and such bubbles have a tendency to cause the user of the dentifrices to choke. This is especially true of small children and total nursing care patients. Foaming bubbles can also cause gastric distress and cramps.

Still another drawback of foaming type dentifrices resides in the rinsing function. As hereinabove stated, most dentifrices include a fluoride therein as a decay reducer and preventative. If left on the surface of the teeth, the fluoride acts to reduce decay. The rinsing of the dentifrice from the mouth with water, however, removes the fluoride, and hence its decay fighting property is reduced.

Because of these and other problems, there have been attempts to alter the basic composition of dentifrices in order to avoid especially the burning and foaming characteristics thereof. For example, an ingestible, non-burning and non-foaming dentifrice has been developed in response to requirement of the Manned Spacecraft Center, National Aeronautics and Space Administration. As is apparent, astronauts in a gravity-free environment are unable to employ the conventional burning and foaming type commercial dentifrices. Thus, the lack of facilities for brushing and rinsing in a spacecraft renders the use of conventional dentifrices impossible.

This new type of dentifrice is formed of a mixture of the following ingredients: insoluble sodium metaphosphate, dicalcium phosphate dihydrate, glycerin, sodium carboxymethylcellulose, saccharin, distilled water and spearmint oil. It is claimed that such a dentifrice composition is ingestible and non-foamy. Nevertheless, such a composition will not achieve effective toothbrushing without the addition of other features. Thus, this dentifrice composition suffers from the disadvantage of the lack of fluoride and compatable abrasives for fighting tooth decay.

Because of this disadvantage, it is proposed, according to the concepts of the present invention, to provide a new decay fighting dentifrice. More particularly, a new dentifrice is provided according to the present invention that is ingestible, non-burning, non-foaming, and which fights tooth decay due to the presence of fluoride and phosphate therein.

It is accordingly an object of the present invention to provide a method of manufacturing a fluoride-acid phosphate-containing dentifrice that is ingestible, non-burning, and non-foaming.

A further object of the present invention is to provide a novel fluoride-containing dentifrice that is ingestible, non-burning and non-foaming.

These and other objects and advantages of this invention will become apparent from the following description.

Despite previous efforts, there has not heretofore been developed any paste dentifrice composition that, in addition to possessing the qualities of being ingestible, non-burning and non-foaming, also fulfills the requirement of being decay preventative by containing as one of its ingredients fluoride and/or acid phosphates.

An example of a typical and known ingestible, non-burning, and non-foaming paste dentifrice useful in the preparation of the decay preventing paste dentifrice according to the present invention comprises a mixture containing insoluble sodium metaphosphate, dicalcium phosphate dihydrate, glycerin, sodium carboxymethylcellulose, saccharin, distilled water and spearmint oil. The metaphosphate and the phosphate dihydrate constituents of the above mixture function as the abrasive ingredient of the dentifrice. Thus, in the brushing operation, these ingredients are responsible for the removal or the prevention of accumulation of stains, tartar and calculus. Referring to the glycerin and the distilled water constituents of the above known paste composition, these ingredients function merely as vehicles. Thus, they are inactive substances in the dentifrice and serve merely as a edium or carrier for the active substances of the dentifrice. In regard to the sodium carboxymethylcellulose material of the dentifrice, this ingredient serves the purpose of a binder. Hence, this holds the solid substances of the dentifrice together in a plastic mass, and this imparts to the paste a quality enabling it to be provided in a tube and squeezed therefrom in use. Referring to the saccharin ingredient, this material, as is obvious, acts to sweeten the dentifrice so as to make it palatable to the taste when in use. The final ingredient of the basic and known ingestible, non-burning and non-foaming dentifrice is spearmint oil. This material adds flavor to the dentifrice and results in a pleasant and refreshing aftertaste to the mouth at the termination of use.

According to the present invention, it has now surprisingly been found that by incorporating into a preparation of the known and general composition above stated, fluoride and acid phosphates in balanced amounts, it is possible to obtain a dentifrice that is not only ingestible, non-burning, and non-foaming, but in addition is capable of fighting or inhibiting decay. This addition of fluoride further provides a unique feature and function with the dentifrice of general composition above stated. Thus, the fluoride will remain on the surface of the teeth since there is no need for rinsing the mouth with water when using the general composition dentifrice. It will readily be seen that the phosphate-fluoride-containing dentifrice of the present invention therefore allows the fluoride to be deposited upon the surface of the teeth, and that once deposited it is not rinsed away. This provides a much more effective decay barrier than the dentifrices commercially available which are adapted to be rinsed from the mouth.

The fluoride-containing paste dentifrice of the present invention is characterized in that it contains as the base composition 34.97% calcium pyrophosphate, 28.8 to 28.9% by weight of glycerin, 1.2 to 1.5% by weight of sodium carboxymethylcellulose, 0.1% by weight of saccharin, 23.3 to 34.6% by weight of distilled water and 1.4% by weight of spearmint oil.

A preferred composition of the base dentifrice of the fluoride-containing preparation according to the present invention is the following expressed in percent by weight:

|  | % by weight |
| --- | --- |
| Calcium pyrophosphate | 34.9 |
| Glycerin | 28.8 |
| Sodium CMC | 1.2 |
| Xylitol | .1 |
| Water | 34.6 |
| Spearmint Oil | .4 |
|  | 100.0 |

This base dentifrice composition as above set forth may in addition to the ingredients specified therein contain an amount of 0.01% by weight of sodium benzoate. This benzoate material functions as a preservative to prevent decomposition of the ingredients of the dentifrice.

The invention is further illustrated by means of the following examples which set forth one mode of preparation of the base dentifrice composition according to my invention.

EXAMPLE I

Into a container was added 7.5 grams of sodium carboxymethylcellulose and 145.0 grams of glycerin. The container was slowly heated to 105° F., accompanied by continuous stirring of the component ingredients therein.

In a separate container was added 117.0 grams of distilled water which was heated to 150° F. To the heated water was added 1.5 grams of saccharin, 230 grams of insoluble calcium pyrophosphate. These component ingredients were mixed with a stirrer for ten minutes.

Into a third container was added the component ingredients of the above two containers along with 2.0 grams of spearmint oil. This composition was stirred mechanically for ten minutes. The resulting base dentifrice composition was suitable for fluoride treatment, as will be described hereinafter.

EXAMPLE II

Into a container was added 50 grams of sodium carboxymethylcellulose and 1160 grams of glycerin. The container was slowly heated to 150° F., accompanied by continuous stirring of the ingredients therein.

In a separate container was added 1390 grams of distilled water which was heated to 150° F. To the heated water was added 4.0 grams of saccharin, 1400 grams of insoluble calcium pyrophosphate. These ingredients were mixed well with a stirrer for ten minutes.

Into a third container was added the ingredients of the above two containers along with 16.0 grams of spearmint oil. This composition was suitable for fluoride treatment, as will be described hereinafter.

The dentifrice compositions set forth above in each of Examples I and II constitute pastes. If it is desired to produce a water free gel-type dentifrice, however, it is merely necessary to substitute an equivalent amount of a suitable gel for the distilled water in each of Examples I and II.

EXAMPLE III

The procedure of Example I was repeated except that 117.0 grams of glycerin was substituted for the 117.0 grams of distilled water. Resulting was a gel-type dentifrice composition suitable for fluoride treatment.

EXAMPLE IV

The procedure of Example II was repeated except that 1390 grams of glycerin was substituted for the 1390 grams of distilled water. Resulting was a gel-type dentifrice base composition suitable for fluoride treatment.

The following examples illustrate modes of procedure for adding phosphates and fluoride to the base dentifrice compositions of Examples I to IV in order to impart to these compositions tooth decay preventing properties.

EXAMPLE V

The procedure of Example I was repeated except that 2.0 grams of sodium fluoride (0.4% by weight) was added to the heated water. Additionally, 5.0 grams of sodium dihydrogen phosphate was added to the third container in order to adjust the pH of the composition to about 3.5 during the mechanical stirring, the fluoride-containing paste dentifrice was allowed to cool, poured into a conventional toothpaste tube, and the end crimped, as is well known in the art.

EXAMPLE VI

The procedure of Example I was repeated except that 5.0 grams of sodium dihydrogen phosphate was added to the third container in order to adjust the pH of the composition to about 3.5 during the mechanical stirring. After the ten minutes of stirring, the paste dentifrice was allowed to cool, poured into a conventional toothpaste tube, and the end crimped, as is well known in the art.

EXAMPLE VII

The procedure of Example I was repeated except that 2.0 grams of stannous fluoride (0.4% by weight) was added to the heated water. Additionally, 5.0 grams of sodium dihydrogen phosphate was added to the third container in order to adjust the pH of the composition to about 3.5 during the mechanical stirring. After the ten minutes of stirring, the fluoride-containing paste dentifrice was allowed to cool, poured into a conventional toothpaste tube, and the end crimped, as is well known in the art.

EXAMPLE VIII

The procedure of Example II was repeated except that 16.0 grams of sodium fluoride (0.4% by weight) was added to the heated water. Additionally, 14.0 grams of sodium dihydrogen phosphate was added to the third container in order to adjust the pH of the composition to about 3.5 during the mechanical stirring. After the ten minutes of stirring, the fluoride-containing paste dentifrice was allowed to cool, poured into a toothpaste tube and crimped.

EXAMPLE IX

The procedure of Example II was repeated except that 14.0 grams of sodium dihydrogen phosphate was added to the third container in order to adjust the pH of the composition to about 3.5 during the mechanical stirring. After the ten minutes of stirring, the fluoride-containing paste dentifrice was allowed to cool, poured into a toothpaste tube and crimped.

EXAMPLE X

The procedure of Example II was repeated except that 16.0 grams of stannous fluoride (0.4% by weight) was added to the heated water. Additionally, 14.0 grams of sodium dihydrogen phosphate was added to the third container in order to adjust the pH of the composition to about 3.5 during the mechanical stirring. After the ten minutes of stirring, the fluoride-containing paste dentifrice was allowed to cool, poured into a toothpaste tube and crimped.

EXAMPLE XI

The procedure of Example III was repeated except that 2.0 grams of sodium fluoride (0.4% by weight) was added to the heated glycerin and sodium carboxymethycellulose mixture. Additionally, 5.0 grams of sodium dihydrogen phosphate was added to the third container in order to adjust the pH of the composition to about 3.5 during the mechanical stirring. After the ten minutes of stirring, the fluoride-containing gel-type dentifrice was allowed to cool without inhibiting flow, poured into a toothpaste tube and the end crimped.

EXAMPLE XII

The procedure of Example IV was repeated except that 16.0 grams of sodium fluoride (0.4% by weight) was added to the heated glycerin. Additionally, 16.0 grams of sodium dihydrogen phosphate was added to the third container in order to adjust the pH of the composition to about 3.5 during the mechanical stirring. After the ten minutes of stirring, the fluoride containing gel-type dentifrice was allowed to cool without inhibiting flow, poured into a toothpaste tube and the end crimped.

While the above examples have been illustrated with regard to acid phosphates for pH adjustment, namely sodium dihydrogen phosphate, it should be apparent that other acid phosphates including orthophosphoric acids and sodium monohydrogen-phosphate are equally useful as pH adjusters. Also, other flavoring agents in addition to spearmint oil are useful; for example, any of chocolate extracts, cinnamon oil, grape, orange oil, banana oil, lemon oil, lime oil, vanilla oil, peppermint oil, etc. Further, inert and artificial coloring agents may be added to the dentifrice compositions disclosed herein to improve the aesthetics thereof. It should also be apparent that the dentifrices according to the present invention may be used in combination with conventional disposable finger applicators as well as the normal toothbrush, the former providing a portable and disposable manner of brushing the teeth.

In addition to sodium fluoride, stannous fluoride or stannous fluoride and sodium fluoride together may be substituted in the gel-type dentifrices of Examples VII and VIII. Since these gel compositions are water free, there is no tendency for the stannous fluoride, which possesses decay preventing properties, to decompose and break down to the inert material stannic fluoride. Thus, as long as the dentifrice composition is water free, as is the case with gel-type compositions, the decay fighting properties of stannous fluoride are preserved.

In order to overcome this property of stannous fluoride to decompose to inert stannic fluoride in water-containing non-compatible abrasive paste-type dentifrices, it is proposed as a further feature of the invention herein to provide a two-component dentifrice product gel-paste-type which contains stannous fluoride in a fashion to retain its decay preventing properties. This two-component gel-paste dentifrice is best illustrated by reference to the following example.

EXAMPLE XIII

The procedure of Example II was repeated except that 16.0 grams of sodium dihydrogen phosphate was added to the third container in order to adjust the pH of the paste dentifrice composition to about 3.5 during the mechanical stirring. After the ten minutes of stirring, the fluoride-free paste composition was allowed to cool and poured into the main dentifrice chamber of a tube of construction similar to that disclosed in U.S. Pat. No. 3,175,731.

Into a fourth container was added 16.0 grams of stannous fluoride (0.4% by weight) and 30.0 grams of glycerin (water free) and sodium carboxymethycellulose mixture. These ingredients were heated to 150° F., mixed well with a mechanical stirrer for ten minutes, allowed to cool without inhibiting flow, and poured into the auxiliary chamber of the tube specified above. The tube end was crimped, thereby isolating the water-containing paste dentifrice component composition from the stannous fluoride water-free gel component. The cap of the tube was removed, and the tube was squeezed. The paste dentifrice was dispensed along with a quantity of the stable stannous flouride gel. It was found that the stannous fluoride did not decompose upon exposure for five minutes, which elapse if time is sufficient for a toothbrushing sequence, whether by means of a toothbrush or a disposable finger applicator. Thus, a convenient and effective phosphate stannous flouride gel paste dentifrice was provided. This isolation procedure of the fluoride from the dentifrice composition may also be used in any case where it is found that any compound such as stannous fluoride, is unstable or may become unstable. This dispensing allowed stannous fluoride and sodium dihydrogen phosphate to react together with the tooth during tooth cleansing.

EXAMPLE XIV

The procedure of Example II was repeated except that 16.0 grams of sodium dihydrogen phosphate was added to the third container in order to adjust the pH of the paste dentifrice composition to about 3.5 during the mechanical stirring. After the ten minutes of stirring, the fluoride-free paste composition was allowed to cool and poured into the main dentifrice chamber of a tube of construction similar to that disclosed in U.S. Pat. No. 3,175,131, the tube being composed of plastic material.

Into a fourth container was added 16.0 grams of stannous fluoride (0.4% by weight), 30.0 grams of glycerin (water-free), sodium carboxymythecellulose and a coated sodium fluoride added to the gel thus producing a gel with stannous fluoride and coated sodium fluoride evenly dispersed within glycerin and sodium carboxymythecellulose mixture. These ingredients were heated to 150° F., mixed well with a mechanical stirrer for ten minutes, allowed to cool without inhibiting flow, and poured into the auxiliary chamber of the tube specified above. The tube end was crimped, thereby isolating the water-containing paste dentifrice component composition from the stannous fluoride water-free gel component. The cap of the tube was removed, and the tube was squeezed. The paste dentifrice was dispensed along with a quantity of the stable stannous fluoride gel. It was found that the stannous fluoride did not decompose upon exposure for five minutes, which elapse if time is sufficient for a tooth brushing sequence, whether by means of a toothbrush or a disposable finger applicator. Thus, a convenient and effective phosphate stannous fluoride gel-paste dentifrice was provided. This isolation procedure of the fluoride from the dentifrice composition may also be used in any case where it is found that any compound such as stannous fluoride, is unstable or may become unstable. This dispensing allowed stannous fluoride and sodium dihydrogen phosphate to react together with the tooth during tooth cleansing.

While the above described dentifrices have been found to be suitable for topical treatment of the teeth, it is also desirable to provide for systemic treatment as well. By topical treatment is meant the action of the fluoride in the mouth, whereas systemic treatment involved the actual absorption of the fluoride into the bloodstream.

In topical treatment, the initiation of the brushing action causes the stannous fluoride compound in the dentifrice to ionize. At the same time, the sodium dihydrogen phosphate component of the dentifrice etches the surface of the teeth to produce an energized tooth surface. A complex stannous fluoride fluorophosphate compound is then provided at the energized tooth surface in order to inhibit tooth decay.

In the systemic treatment, however, the fluoride is absorbed by the mucosa lining of the stomach as the ingestible dentifrice containing fluoride is swallowed, and thereby fluoride is actually introduced into the bloodstream. The fluoride will eventually work itself into the salivary glands and it should be apparent that there will be provided after a period of time a continual bathing of the teeth in a very dilute fluoride salivary solution.

The systemic fluoride treatment also allows fluoride to be incorporated into the structure of the tooth during the normal development of the tooth by entry into the tooth bud itself. As the fluoride is absorbed systematically into the bloodstream, it passes to the tooth bud during development. Here, the fluoride combines with the hydroxy-apatite moiety of the enamel and the dentin to form a fluorohydroxy apatite moiety which is resistant to tooth decay. Such systemic treatment therefore results in a tooth totally resistant to tooth decay, whereas as noted hereinbefore, the topical treatment is primarily a surface phenomenon.

It has been found in systemic treatment, that the fluoride can only be absorbed in an acid medium. This acid medium is provided by the organ of the stomach where acids are produced by the stomach glands. The other portions of the digestive tract such as the intestines are basic, however, and therefore the stomach is the primary zone for systemic fluoride absorption.

A major problem with systemic treatment has been the relatively short residence time of the fluoride in the stomach for absorption into the bloodstream. This is for the reason that the digestive process taking place in the stomach empties the stomach too rapidly without allowing sufficient bloodstream absorption time for the fluoride. It has been found, however, in accordance with the present invention that the residence time of the fluoride in the stomach may be substantially increased by coating the fluoride compound with a lipid and/or gelatin-like material. The lipid compounds undergo slower digestion in the stomach and act as a timed release mechanism for the fluoride. The fluoride dwell time in the stomach is therefore increased and is released from the lipid over a sustained period of time in the stomach thereby providing a greater opportunity for the fluoride to be absorbed in the bloodstream. It has been found, for example, that the lipid will gradually dissolve over a period of several hours thus providing an increased residence time of fluoride in stomach and a sustained release thereof.

Suitable lipids that have been found useful in accordance with the present invention are fats and fatty oils such as glycerides, neutral esters of glycerol and saturated and unsaturated fatty acids; essential oils such as terpenes, aldehydes, and alcohols; waxes such as esters of sterols and fatty acids; phosphatides such as lecithins; glycolipins such as cerebton and phrenosin; sulfolipins such as protogon and brain-sulfatide; aminolipins as bregenin; and chromolipins as lipchromes.

The fluoride compound most suited for systemic treatment has been found to be sodium fluoride coated with a suitable lipid or gelatin-like compound. Stannous fluoride does not absorb sufficiently systemically and therefore it is primarily best suited for topical treatment. As the coated sodium fluoride is swallowed with the ingestible dentifrice, however, the coating dissolves and the sodium fluoride is freed for eventual absorption into the bloodstream. It has also been shown that the sodium dihydrogen phosphate component not only exhibits a topical anticaries effect on the teeth but also systemically presumably by the absorption from the gastrointestinal tract into the blood stream and through the saliva from the salivary glands.

An additional perfecting feature of the present invention is the substitution of xylitol for the saccharin component in the above described examples. Xylitol ($C_5H_{12}O_5$) is a pentahydric alcohol derived from wood sugar and possesses the unique feature as a sugar in that it is not digested in the mouth. Rather, xylitol is digested in the stomach which means that it never enters into any type of tooth decay mechanism in the mouth. Since the sweetness of xylitol is slightly greater than sugar it may be readily substituted therefor beside possessing the advantage of stomach digestion as contrasted with conventional sugars which are digested in the mouth and cover the surface of the teeth causing decay and plaque. Accordingly and as noted above, xylitol may be substituted in any of the above examples for the saccharin component of the various dentifrice composition set forth therein.

In order to illustrate the concept of a topical-systemic ingestible dentifrice, the following example is set forth.

EXAMPLE XV

Into a container was added 50 grams of sodium carboxymethylcellulose and 1160 grams of glycerin. The container was slowly heated to 150° F., accompanied by continuous stirring of the ingredients therein.

In a separate container was added 1390 grams of distilled water which was heated to 150° F. To the heated water was added 4.0 grams of xylitol and 1400 grams of calcium pyrophosphate. These ingredients were mixed well with a stirrer for ten minutes.

Into a third container was added and mixed the ingredients of the above two containers along with 16.0 grams of spearmint oil.

Into the third container was added 16.0 grams of sodium dihydrogen phosphate in order to adjust the pH of the paste dentifrice composition to about 3.5 during the mechanical stirring. After ten minutes of stirring, the acid-phosphate paste composition was allowed to cool and poured into the main dentifrice chamber of a two-part toothpaste tube of construction similar to that disclosed in U.S. Pat. No. 3,175,731.

Into a fourth container was added 16.0 grams of stannous fluoride and 8 grams coated sodium fluoride (0.4% by weight) and 3.0 grams of glycerin (water-free) and sodium carboxymethylcellulose. These ingredients were heated to 150° F., mixed well with a mechanical stirrer for ten minutes, allowed to cool without inhibiting flow, and poured into the auxiliary chamber of the two-part tube specified above. The tube end was crimped, thereby isolating the water-containing acid-phosphate paste dentifrice component composition from the stannous fluoride and systemic sodium fluoride water-free gel component. The cap of the tube was removed, and the tube was squeezed. The paste dentifrice was dispensed along with a quantity of the stable fluoride gel.

It was found that the resulting dentifrice provided both topical treatment as hereinbefore described as well as systemic treatment. Both types of treatment resulted whether the dentifrice was applied by means of a toothbrush or by means of a disposable finger applicator as generally shown for example in U.S. Pat. No. 3,952,867.

Although specific embodiments have been described in detail hereinbefore, it is understood that the subject invention is not limited thereto, and all obvious variations and modifications thereof are contemplated and are included within the spirit and scope of the invention as defined in the appended claims.

What is claimed is:

1. A dentifrice composition for topical fluoride treatment of human teeth during oral hygiene, said dentifrice composition comprising:

a quantity of stannous fluoride sufficient to develop a fluoride concentration of said composition from about 0.03% to about 0.05% by weight of said dentifrice composition;

a sufficient quantity of sodium dihydrogen phosphate compound for pH adjustment to a pH range of about 3.5 and for developing an energized tooth surface for enhancement of said topical fluoride treatment, said stannous fluoride and said sodium dihydrogen phosphate providing a complex stannous fluoride fluorophosphate compound at the energized tooth surface during oral hygiene that develops a caries inhibiting fluorophosphate complex within the crystalline latticework of the tooth enamel; and a water-free gel carrier that inhibits deterioration of the stannous fluoride and the sodium dihydrogen phosphate compound prior to use in an aqueous environment.

* * * * *